| United States Patent [19] | [11] 4,172,142 |
|---|---|
| Merkel et al. | [45] Oct. 23, 1979 |

[54] PROCESS FOR PREPARING PYRROLO-BENZOIC ACID DERIVATIVES

[75] Inventors: Wulf Merkel, Bad Soden am Taunus; Dieter Bormann; Dieter Mania, both of Kelkheim; Roman Muschaweck, Frankfurt am Main, all of Fed. Rep. of Germany

[73] Assignee: Hoechst Aktiengesellschaft, Frankfurt am Main, Fed. Rep. of Germany

[21] Appl. No.: 862,669

[22] Filed: Dec. 21, 1977

[30] Foreign Application Priority Data

Dec. 24, 1976 [DE] Fed. Rep. of Germany ....... 2658766
Apr. 26, 1977 [DE] Fed. Rep. of Germany ....... 2718494

[51] Int. Cl.$^2$ ............................................. A61K 31/40
[52] U.S. Cl. ................................ 424/274; 260/326.41
[58] Field of Search .................... 260/326.41; 424/274

[56] References Cited

U.S. PATENT DOCUMENTS 4,010,273  3/1977  Bormann et al. ............... 260/326.41

Primary Examiner—Donald G. Daus
Assistant Examiner—D. B. Springer
Attorney, Agent, or Firm—Curtis, Morris & Safford

[57] ABSTRACT

Salidiuretically-active 3-pyrrolo-5-sulfamoylbenzoic acids having a methylphenoxy or chlorophenoxy group substituted in the 4-position, and alkyl esters thereof, are disclosed, as are methods of making and using the same.

2 Claims, No Drawings

PROCESS FOR PREPARING PYRROLO-BENZOIC ACID DERIVATIVES

The present invention provides a process for preparing pyrrolo-benzoic acid derivatives of the formula I

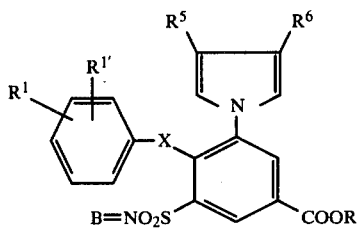

wherein R represents hydrogen or alkyl with 1-4 carbon atoms, $R^1$ and $R^{1'}$ represent hydrogen, halogen, $CF_3$, alkyl or alkoxy groups with 1-4 carbon atoms, optionally protected hydroxy or amino groups in various positions of the ring or in combination represent the 3,4-methylene dioxy group, B stands for 2 hydrogen atoms or the group

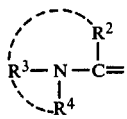

in which $R^2$, $R^3$ and $R^4$ represent lower alkyl groups, $R^2$ may also represent hydrogen, and/or any two of the substituents $R^2$, $R^3$ and $R^4$ may also be connected to form a cycle, $R^5$ and $R^6$ may be identical or different and represent hydrogen or alkyl with 1 to 2 carbon atoms and X represents O, S, NH or $CH_2$, as well as the pharmaceutically acceptable salts thereof with bases and acids, which comprises reacting 3-amino-substituted benzoic acid derivatives of the formula II

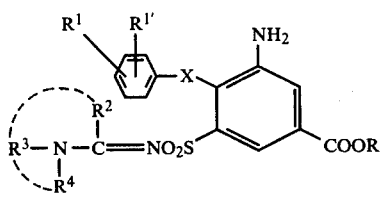

wherein R to $R^4$ and X have the afore given meanings with 2,5-dialkoxy tetrahydrofuranes of formula III

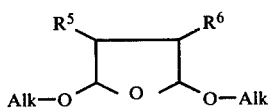

wherein the radicals $R^5$ and $R^6$ have the aforementioned meanings and Alk stands for an alkyl group with 1 to 4 carbon atoms (preferably methyl), and, if desired to obtain compounds of formula I wherein B represents 2 hydrogen atoms subsequently hydrolyzing the compounds obtained.

The starting compounds of formula II are partially known from German Offenlegungsschrift No. 2,461,601 or they are prepared analogously. The reaction of the amines II is mostly carried out in weak organic acids, preferably in glacial acetic acid, at boiling temperature.

The presence of the protective group at the sulfamoyl function increases the yield considerably, in comparison to the analogous reaction in the presence of a free sulfamoyl group, as known from Belgian Pat. No. 828,441, and enables almost quantitative yields.

The compounds of formula I in which B represents the sulfonamide protective group are interesting intermediate products for the preparation of medicaments, especially for preparing diuretics such as described in Belgian Pat. No. 828,441. These compounds carrying in 3-position a corresponding pyrrolidine ring substituted by $R^5$, $R^6$, are obtained by catalytic hydrogenation, for example by means of noble metal catalysts such as Pd/active carbon, $PtO_2$, Rh/carbon or Pt/active carbon. The reduction may as well be carried out with different reducing agents known for pyrroles, such as zinc/glacial acetic acid or hydriodic acid and red phosphorus.

After the reduction an acid or alkaline hydrolysis is carried out for splitting off the sulfonamide protective group and optionally the ester radical R.

It could not have been expected that the compounds of formula I would be suitable for preparing the pyrrolidino compounds, for fear of the protective group of the sulfonamide radical being also affected under the hydrogenation conditions necessary for the pyrrole radical.

If $R^1$ and $R^{1'}$ mean OH groups and/or $NH_2$ groups, those may be protected in compounds of formula II by the benzyl radical.

Numerous interesting intermediate products of formula I can be prepared according to the process of the invention. Besides the compounds mentioned in the following Examples there may also be prepared the compounds specified below:

4-Phenoxy-3(1-pyrrolo)-5-N,N-dimethylamino-methylene aminosulfonyl-benzoic acid 4-(4'-Methylenephenoxy)-3(1-pyrrolo)-5-N,N-dimethylamino-methylene-amino-sulfonyl-benzoic acid ethyl ester 4-(3'-Methylphenoxy)3-(1-pyrrolo)-5-N,N-dimethylamino-methylene-amino-sulfonylbenzoic acid methyl ester 4-(3'-Methoxyphenoxy)-3(1-pyrrolo)-5-N,N-dimethylamino-methylene-amino-sulfonylbenzoic acid butyl ester 4-(3'-Hydroxyphenoxy)-3(1-pyrrolo)-5-N,N-dimethylamino-methylene-amino-sulfonylbenzoic acid methyl ester 4-(4'-Methylphenoxy)-3(3'-Methyl-1-pyrrolo-5-N,N-dimethylamino-methylene-amino-sulfonyl-benzoic acid methyl ester 4-Phenoxy-3(3'-methyl-1-pyrrolo)-5-N,N-dimethylamino-methylene-amino-sulfonylbenzoic acid ethyl ester 4-Benzyl-3(1-pyrrolo)-5-N,N-dimethylamino-methylene-aminosulfonyl-benzoic acid 4-(4'-Methylbenzyl)-3(1-pyrrolo)-5-N,N-dimethylamino-methylene-amino-sulfonylbenzoic acid methyl ester 4-Benzyl-3(3'-methyl-1-pyrrolo)-5-N,N-dimethylamino-methylene-amino-sulfonyl-benzoic acid methyl ester 4-(4'-Methylbenzyl)3(3'-methyl-1-pyrrolo)-5-N,N-dimethylamino-methylene-amino-sulfonylbenzoic acid methyl ester 4-(4'-Chlorobenzyl)-3(1-pyrrolo)-5-N,N-dimethylamino-methylene-amino-sulfonylbenzoic acid methyl ester 4-(4'-Methylanilino)-3(1-pyrrolo)-5-N,N-dimethylamino-methylene-amino-sulfonylbenzoic acid methyl ester 4-(4'-Methoxyanilino)-3(1-pyrrolo)-5-N,N-dimethylamino-methylene-amino-sulfonylbenzoic acid methyl ester 4-(3'-Methoxyanilino)-3(1-pyrrolo)-5-N,N-dimethylamino-methylene-amino-sulfonylbenzoic acid ethyl ester 4(4'-Chloroanilino)-3(1-pyrrolo)-5-N,N-dimethylamino-methylene-amino-sulfonylbenzoic acid butyl ester 4-(4'-Fluoranilino)-3(1-pyrrolo)-5-N,N-dimethylamino-methylene-amino-sulfonylbenzoic acid methyl ester 4-(4'-Methylanilino)-3-(3'-methyl-1-pyrrolo)-5-N,N-dimethylamino-methylene-amino-sulfonylbenzoic acid methyl ester 4-(4'-Chloranilino)-3-(3'-methyl-1-pyrrolo)-5-N,N-dimethylamino-methylene-amino-sulfonylbenzoic acid methyl ester The present invention also provides compounds of the formula IV

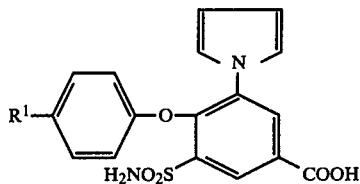

IV as well as the lower alkyl esters thereof, wherein $R^1$ represents methyl or chlorine. These compounds are obtained by acid or alkaline hydrolysis of the compounds of formula I wherein B represents the sulfonamide protective group. Optionally the free carboxylic acids of formula IV obtained are esterified subsequently in usual manner. The compounds of formula IV show surprisingly highly efficient diuretic and saluretic properties; this could not be expected, since the corresponding non-substituted compound of formula IV ($R^1=H$) exhibits weakly diuretic properties only and is surpassed in that respect many times by the 4-chloro-substituted or 4-methyl-substituted compounds.

The sulfamoylbenzoic acid derivatives of formula IV and the pharmaceutically acceptable salts thereof may be used as medicaments in humane or veterinary medicine. They are administered in doses of 0.5 to 100 mg in capsules, dragees, tablets or solutions with various additives, by enteral or oral way by stomach tube or similar devices, or by parenteral administration (injection in the vascular system, e.g. intraveneously or intramuscularly, or subcutaneously). They are suitable for treating edema such as edema due to cardiac, renal or hepatic diseases, and other such diseases due to disorders of the water and electrolyte balance. The compounds may be used alone or in combination with other substances having salidiuretic or other actions or they may be administered with various other medicaments either separately, in alternation or in combination. There may be cited especially spironolactone, triamterene, amiloride, and other compounds retaining $K^+$ alternatingly with long-acting salidiuretics of the chlorthalidone type or other compounds containing potassium and substituting a loss in $K^+$ (salts etc.). The following Examples illustrate the invention:

EXAMPLE 1

3-N-pyrrolo-4-phenoxy-5-N,N-dimethylaminomethylene aminosulphonyl-benzoic acid methyl ester 100 g of 3-amino-4-phenoxy-5-N,N-dimethylaminomethylene aminosulfonyl benzoic acid methyl ester and 53 g of 2,5-dimethoxytetrahydrofurane are refluxed for 15 minutes in 100 g of glacial acetic acid. The mixture is cooled to 10° C., the precipitated crystals are vacuum filtered, washed with 20 ml of cold glacial acetic acid and dried in vacuo.

There are obtained 96 g of colorless to brownish crystals having a melting point of 173°–175° C.

For further purification, another recrystallization may be carried out, if necessary, from isopropanol or acetic acid ethyl ester.

Conversion to 4-phenoxy-3(1-pyrrolidinyl)-5-sulfamoyl-benzoic acid 10 g of 3-N-pyrrolo-4-phenoxy-5-N,N-dimethylaminomethyleneamino sulfonyl-benzoic acid methyl ester are hydrogenated for 5 hours at 100° C. and under a pressure of 100 atm. in 100 ml of methanol and with the addition of 1 g of palladium/charcoal (at 10%). The catalyst is filtered off while hot. 8 g of 4-phenoxy-3(1-pyrrolidinyl)-5-N,N-dimethylaminomethyleneamino-sulfonyl-benzoic acid methyl ester melting at 187°–189° C. crystallize from the solution upon cooling.

The product thus obtained is suspended in 100 ml of 2 N sodium hydroxide solution and refluxed until the solution is limpid. The free 4-phenoxy-3(1-pyrrolidinyl)-5-sulfamoyl-benzoic acid precipitates on acidification with 2 N hydrochloric acid to a pH of 3–4.

Recrystallization from $CH_3OH/H_2O$.

Light yellow crystals melting at 226°–228° C.

EXAMPLE 2

3-N-pyrrolo-4-(4'-methylphenoxy)-5-N,N-dimethylaminomethylene-amino-sulfonyl-benzoic acid methyl ester (a)

3-nitro-4-(4'-methylphenoxy)-5-N,N-dimethylaminomethylene amino-sulfonyl-benzoic acid methyl ester A solution of 235 g (0.67 mole) of 3-nitro-4-chloro-N,N-dimethylamino methylene aminosulfonyl benzoic acid methyl ester and 140 g (0.96 mole) of potassium-4-methylphenolate in 1 ltr. of absolute dimethylformamide (DMF) is stirred at 90°–100° C. for 2 hours. The cold solution is then added slowly and dropwise to 4–5 l of ice water while stirring vigorously. The precipitated product is vacuum filtered, washed with $H_2O$ and recrystallized from $CH_3OH$. There are obtained light yellow crystals having a melting point of 200°–201° C.

(b)

3-amino-4-(4'-methylphenoxy)-5-N,N-dimethylaminomethylene amino-sulfonyl-benzoic acid methyl ester 171 g of 3-nitro-4-(4'-methylphenoxy)-5-N,N-dimethylaminomethylene aminosulfonyl-benzoic acid methyl ester are hydrogenated with Raney nickel as a catalyst in dimethyl formamide at 50° C. and under 50 atm. pressure for 8 hours in an autoclave. The result is then filtered, the filtrate is condensed and the residue recrystallized from CH₃OH. There are obtained colorless crystals having a melting point of 172°–173° C.

3-N-pyrrolo-4-(4'-methylphenoxy)-5-N,N-dimethylaminomethylene-amino-sulfonyl-benzoic acid methyl ester 19.5 g (0.05 mole) of 3-amino-4-(4'-methylphenoxy)-5-N,N-dimethyl aminomethylene aminosulfonyl benzoic acid methyl ester and 7 ml (~0.075 mole) of 2.5-dimethoxytetrahydrofurane are refluxed in 150 ml of glacial acetic acid.

After a reaction time of one hour the mixture is introduced dropwise into ice water. The precipitated light-brown product is vacuum filtered and recrystallized from CH₃OH/acetone (the latter in a minor quantity).

There are obtained 17.5–18 g, having a melting point of 178°–179° C.

EXAMPLE 3

3-N-pyrrolo-4-(4'-methoxyphenoxy)-5-N,N-dimethylaminomethylene-aminosulfonyl benzoic acid methyl ester (a)

3-nitro-4-(4'-methoxyphenoxy)-5-N,N-dimethylaminomethyleneamino-sulfonyl benzoic acid methyl ester 0.4 mole (126 g) of 3-nitro-4-chloro-5-N,N-dimethylaminomethylene-aminosulfonyl benzoic acid methyl ester and 72.5 g (~0.5 mole) of sodium-4-methoxyphenolate are refluxed in 600 ml of absolute DMF for 2 hours. The reaction mixture is then stirred into 4 l of ice water and the precipitated product is vacuum filtered. Light yellow crystals having a melting point of 199°–201° C. are obtained on recrystallization from CH₃OH.

(b)

3-amino-4-(4'-methoxyphenoxy)-5-N,N-dimethylaminomethylene-amino-sulfonyl benzoic acid methyl ester The reaction is carried out analogously to the process described in Example 2b. By recrystallization from CH₃OH there are obtained colorless crystals having a melting point of 141°–143° C.

(c)

3-N-pyrrolo-4-(4'-methoxyphenoxy)-5-N,N-dimethylamino-methylene-aminosulfonyl benzoic acid methyl ester 20.37 g (0.05 mole) of 3-amino-4-(4'-methoxyphenoxy)-5-N,N-dimethylaminomethylene aminosulfonyl benzoic acid methyl ester and 7 ml of 2,5-dimethoxytetrahydrofurane are refluxed in 150 ml of glacial acetic acid for about one hour. The cold mixture is then stirred into ice water, the precipitated product vacuum filtered and washed with water. There are obtained 20.8 g of crude product.

The crude product may be used as intermediate product without undergoing any additional purification process, i.e., the crude product may be hydrogenated catalytically and hydrolyzed, as described in the specification.

EXAMPLE 4

3-N-pyrrolo-4-(3'-methoxyphenoxy)-5-N,N-dimethylamino methylene aminosulfonyl benzoic acid methyl ester (a)

3-nitro-4-(3'-methoxyphenoxy)-5-N,N-dimethylaminomethyleneaminosulfonyl benzoic acid methyl ester In analogy to Example 3a, however carried out with sodium-3-methoxyphenolate and with a reaction time of 3 hours. Light yellow crystals having a melting point of 201° C. are obtained from glycol monomethyl ether.

(b)

3-amino-4-(3'-methoxyphenoxy)-5-N,N-dimethylaminomethyleneaminosulfonyl benzoic acid methyl ester In analogy to Example 2b, with recrystallization from glycol monomethyl ether, colorless crystals having a melting point of 176°–178° C.

(c)

3-N-pyrrolo-4-(3'-methoxyphenoxy)-5-N,N-dimethylaminomethylene aminosulfonyl benzoic acid methyl ester 12.7 g (0.03 mole) of 3-amino-4-(3'-methoxyphenoxy)-5-N,N-dimethylaminomethylene aminosulfonyl benzoic acid methyl ester and 4.6 ml of 2,5-dimethoxytetrahydrofurane are refluxed for 30 minutes in 150 ml of glacial acetic acid. The product is then precipitated by stirring it into 1.5 l of ice water and recrystallized from CH₃OH/H₂O. There are obtained beige crystals having a melting point of 165°–166° C.

EXAMPLE 5

3-N-pyrrolo-4-(4'-chlorophenoxy)-5-N,N-dimethylaminomethylene-aminosulfonyl-benzoic acid methyl ester (a)

3-nitro-4-(4'-chlorophenoxy)-5-N,N-dimethylaminomethyleneaminosulfonyl-benzoic acid methyl ester A solution of 164 g of 3-nitro-4-chloro-5-N,N-dimethylamino-methylene aminosulfonyl benzoic acid methyl ester and 117 g of potassium-p-chlorophenolate in 800 ml of freshly distilled DMF is refluxed for 2–3 hours. The reaction mixture is added dropwise while stirring vigorously into 4 times its quantity of icewater. The resulting product is separated and boiled with CH₃OH/acetone. Melting point: 227°–228° C.

(b)

3-amino-4-(4'-chlorophenoxy)-5-N,N-dimethylaminomethyleneamino-sulfonyl benzoic acid methyl ester 130 g of the nitro compound (5a) are hydrogenated in 1 ltr. of DMF with Raney-nickel for nine hours, under a pressure of 50 atmospheres and at a temperature of 50° C. After the Raney nickel is removed by filtration, the solution is concentrated and the residue boiled with CH₃OH. There is obtained a colorless substance having a melting point of 207°–208° C.

(c)

3-N-pyrrolo-4-(4'-chlorophenoxy)-5-N,N-dimethylaminomethylene-aminosulfonylbenzoic acid methyl ester 20.6 g of the amino compound (5b) are refluxed for one hour in 150 ml of glacial acetic acid with 7 ml of 2,5-dimethoxy-tetrahydrofurane. The substance is then precipitated by introducing the reaction mixture into 1.5 l of ice water, the precipitate is filtered off and recrystallized from CH₃OH. There are obtained light brown crystals having a melting point of 165° C.

EXAMPLE 6

3-N-pyrrolo-4-(4'-fluorophenoxy)-5-N,N-dimethylaminomethylene aminosulfonyl benzoic acid methyl ester (a)

3-nitro-4-(4'-fluorophenoxy)-5-N,N-dimethylaminomethyleneamino-sulfonyl benzoic acid methyl ester A solution of 210 g (0.6 mole) of 3-nitro-4-chloro-5-N,N-dimethylaminoethylene aminosulfonyl benzoic acid methyl ester and 120 g of sodium-4-fluorophenolate in 800 ml of absolute DMF is stirred at 120°–130° C. for 3–4 hours. The cold solution is then slowly added dropwise into 4–5 l of ice water while stirring vigorously. The precipitated product is filtered off, washed thoroughly with water digested with acetone under heat and then recrystallized from glycol monomethyl ether. There are obtained light yellow crystals having a melting point of 224°–225° C.

(b)

3-amino-4-(4'-fluorophenoxy)-5-N,N-dimethylaminomethylene amino-sulfonyl benzoic acid methyl ester 140 g of the nitro compound (6a) are dissolved in DMF and hydrogenated in the presence of Raney nickel at 50° C. and under a pressure of 50 atmospheres for 8 hours. The Raney nickel is then filtered off and the solution is added dropwise to ice water. The precipitated substance is separated and then washed consecutively with CH₃OH and ether. The practically pure substance may be recrystallized from glycol monomethyl ether. There are obtained colorless crystals having a melting point of 234°–236° C.

(c)

3-N-pyrrolo-4-(4'-fluorophenoxy)-5-N,N-dimethylaminomethylene-aminosulfonyl benzoic acid methyl ester 17.5 g of "amine ester" (7b) and 6.5 ml of 2,5-dimethyoxytetrahydrofurane are refluxed in 150 ml of glacial acetic acid for about one hour. The mixture is then added dropwise to 1.5 l of ice water and the precipitated product is filtered and recrystallized from CH₃OH. There are obtained light brown crystals having a melting point of 180° C.

EXAMPLE 7

3-N-pyrrolo-4-phenylthio-5-N,N-dimethylaminomethylene aminosulfonyl benzoic acid methyl ester 15.8 g of 3-amino-4-phenylthio-5-N,N-dimethylaminomethylene aminosulfonyl benzoic acid methyl ester and 9.2 g of 2,5-dimethoxy-tetrahydrofurane are refluxed for half an hour in 150 ml of glacial acetic acid. By introducing the mixture into ice water the product precipitates and may be digested with hot CH₃OH while it is still damp. The residue is recrystallized from glycol monomethyl ether. There are obtained light yellow crystals having a melting point of 210°–211° C.

EXAMPLE 8

3-N-pyrrolo-4-(4'-methylphenylthio)-5-N,N-dimethylaminomethylene-aminosulfonyl benzoic acid methyl ester (a)

3-nitro-4-(4'-methylphenylthio)-5-N,N-dimethylaminomethylene-aminosulfonyl benzoic acid methyl ester A suspension of 70 g of 3-nitro-4-chloro-5-N,N-dimethylaminomethylene aminosulfonyl benzoic acid methyl ester in 450 ml of absolute DMF is prepared and heated to 80° C. To this suspension is slowly added dropwise a solution of 40 g of potassium-p-thiocresolate in 400 ml of absolute DMF while stirring at 80° C. for two hours. The mixture is then introduced into 4 l of ice water while stirring is continued, the precipitated product is filtered off, washed thoroughly with water and recrystallized from glacial acetic acid. There are obtained yellow crystals melting at 163°–164° C.

(b)

3-amino-4-(4'-methylphenylthio)-5-N,N-dimethylaminomethylene-aminosulfonyl benzoic acid methyl ester 67.7 g of 3-nitro-4-(4'-methylphenylthio)-5-N,N-dimethylamino-methylene aminosulfonyl benzoic acid methyl ester are dissolved in 800 ml of absolute DMF, Raney nickel is added and hydrogen is introduced for 8 hours at 50° C. and under a pressure of 50 atmospheres. After the catalyst has been separated, the solution is stirred into 2 l of ice water and the precipitated product is isolated. By recrystallization from CH₃OH (adding active coal) there are obtained colorless crystals melting at 179° C.

(c)

3-N-pyrrolo-4-(4'-methylphenylthio)-5-N,N-dimethylaminomethylene-aminosulfonyl benzoic acid methyl ester 18.3 g of "amine ester" (8b) are dissolved in 150 ml of glacial acetic acid and heated to the boiling point. 7 ml of 2,5-dimethoxy-tetrahydrofurane are then added. Suddenly, after about 10 minutes, the product crystallizes. Stirring under reflux is continued for another 15 minutes, the precipitated crystals are filtered off in the cold and washed with glacial acetic acid. There are obtained light yellow crystals melting at 242°–243° C.

EXAMPLE 9

3-N-pyrrolo-4-(4'-benzyloxyphenoxy)-5-N,N-dimethylaminomethylene aminosulfonyl benzoic acid methyl ester (a)

3-nitro-4-(4'-benzyloxyphenoxy)-5-N,N-dimethylaminomethylene-aminosulfonyl benzoic acid methyl ester 87.5 g (0.25 mole) of 3-nitro-4-chloro-5-N,N-dimethylaminomethylene-aminosulfonyl benzoic acid methyl ester ae dissolved in 500 ml of anhydrous dimethyl formamide and 77.5 g (0.35 mole) of sodium-4- benzyloxyphenolate are added. While stirring vigorously, the reaction mixture is refluxed for 3–4 hours. After cooling, the turbid solution is added dropwise into 3 l of ice water. The yellow precipitate is vacuum filtration, washed thoroughly with water and recrystallized from methanol. There are obtained 94 g of 3-nitro-4-(4'-benzyloxyphenoxy)-5-N,N-dimethylaminomethylene aminosulfonyl benzoic acid methyl ester as yellow crystals melting at 132° C.

(b)
3-amino-4-(4'-benzyloxyphenoxy-5-N,N-dimethylaminomethylene-aminosulfonyl benzoic acid methyl ester 94 g of 3-nitro-4-(4'-benzyloxyphenoxy)-5-N,N-dimethylaminomethylene-aminosulfonyl benzoic acid methyl ester are dissolved in 1.5 ltr. of dimethyl formamide and, in the presence of Raney nickel, hydrogenated at room temperature and under normal pressure for 6–7 hours. Filtering follows and the limpid solution is introduced dropwise into ice water. The precipitated 3-amino-4-(4'-benzyloxyphenoxy)-5-N,N-dimethylaminomethylene-aminosulfonyl benzoic acid methyl ester is recrystallized from methanol. There are obtained about 70 g of white crystals melting at 170° C.

(c)
3-N-pyrrolo-4-(4'-benzyloxyphenoxy)-5-N,N-dimethylaminomethylene-aminosulfonyl benzoic acid methyl ester 43.5 g of "amine ester" (9b) and 13 ml of 2,5-dimethoxytetrahydrofurane are refluxed for one hour in 250 ml of glacial acetic acid. The product is then precipitated by pouring the reaction mixture into ice water. The precipitate is filtered off, washed with H₂O, and recrystallized from CH₃OH (adding active coal). Melting properties: The product sinters at 80° C., converts to a highly viscous oil which reaches its best fluidity rate at 105°–110° C.

EXAMPLE 10

3-N-pyrrolo-4-anilino-5-N,N-dimethylaminomethylene aminosulfonyl benzoic acid methyl ester (a) 3-nitro-4-anilino-5-N,N-dimethylaminomethylene aminosulfonyl benzoic acid methyl ester 52.5 g of 3-nitro-4-chloro-5-N,N-dimethylaminomethylene aminosulfonyl benzoic acid methyl ester are dissolved in 360 ml of absolute DMF and heated to 100° C. 18 ml of aniline are then added dropwise while stirring and the reaction mixture is maintained at 100° C. for three hours. The product is precipitated by introducing the solution into 2 ltr. of ice water, isolated and washed thoroughly with water. For purifying the product it is boiled with 250 ml of CH₃OH and a minor quantity of acetone. There are obtained crystals melting at 182°–183° C.

(b) 3-amino-4-anilino-5-N,N-dimethylaminomethylene aminosulfonyl benzoic acid methyl ester 40.7 g of "nitro ester" (10a) are dissolved in 600 ml of DMF and hydrogenated for 8 hours in the presence of Raney-nickel as catalyst at 50° C. and under a pressure of 50 atmospheres. The filtered solution is introduced into 2 ltr. of ice water while stirring. The precipitated product is isolated and recrystallized from glycol monomethyl ether. There are obtained colorless crystals melting at 227°–228° C.

(c)
3-N-pyrrolo-4-anilino-5-N,N-dimethylaminomethylene aminosulfonyl benzoic acid methyl ester 11.3 g of "amine ester" (10b) are dissolved in 130 ml of glacial acetic acid and 4.5 ml of 1,2-dimethoxy-tetrahydrofurane are added. After refluxing for 15 minutes, the mixture is stirred into 500 ml of ice water. The precipitated product is isolated and washed several times with water. Finally it is recrystallized from CH₃OH/C₂H₅OH, melting point: 185° C.

EXAMPLE 11

3-N-pyrrolo-4-(3',4'-methylene dioxyphenoxy)-5-N,N-dimethylaminomethylene-aminosulfonyl benzoic acid methyl ester (a)
3-nitro-4-(3',4'-methylenedioxyphenoxy)-5-N,N-dimethylamino-methylene aminosulfonyl benzoic acid methyl ester 96 g of 3-nitro-4-chloro-5-N,N-dimethylaminomethylene aminosulfonyl benzoic acid methyl ester and 58 g of sodium-3,4-methylene dioxyphenolate are blended with 500 ml of absolute DMF and stirred at 120° C. for 2 hours. The mixture is introduced into 4 ltr. of ice water, while stirring is continued. The precipitated light yellow product, separated and recrystallized from n-butanol or CH₃OH/acetone, has a melting point of 216°–217° C.

(b) 3-amino-4-(3',4'-methylene dioxyphenoxy)-5-N,N-dimethylamino-methylene aminosulfonyl benzoic acid methyl ester 76 g of the nitro compound described in Example 11a are dissolved in about 500 ml of absolute DMF and hydrogenated for 8 hours in the presence of Raney nickel as catalyst, at room temperature and under pressure of 50 atmospheres. The filtered solution is then introduced dropwise into ice water and the precipitated product is recrystallized from CH₃OH after the separation. There are obtained colorless crystals melting at 190°–191° C.

(c) 3-N-pyrrolo-4-(3',4'-methylene dioxyphenoxy)-5-N,N-dimethylamino-methylene aminosulfonyl benzoic acid methyl ester 11.5 g of "amine ester" (Example 11b) are refluxed for 1 hour in combination with 4 ml of 2,5-dimethoxytetrahydrofurane in 150 ml of glacial acetic acid. The product is precipitated by introducing the solution dropwise into 1.5 ltr. of ice water and recrystallized from glycol monomethyl ester, melting point: 206° C.

EXAMPLE 12

3-N-pyrrolo-4-(4'-methylanilino)-5-N,N-dimethylaminomethylene-aminosulfonyl benzoic acid methyl ester (a)
3-nitro-4-(4'-methylanilino)-5-N,N-dimethylaminomethylene aminosulfonyl benzoic acid methyl ester 0.2 mole of 3-nitro-4-chloro-5-N,N-dimethylaminomethylene aminosulfonyl benzoic acid methyl ester is dissolved in 500 ml of dimethylformamide at 100° C. and a solution of 0.33 mole of p-toluidine in 200 ml of absolute DMF is added dropwise. After 4 hours the mixture is stirred into ice water and the precipitated product is separated. By recrystallization from CH₃OH there are obtained yellow crystals melting at 210° C.

(b)

3-amino-4-(4'-methylaniline)-5-N,N-dimethylaminomethylene-aminosulfonyl benzoic acid methyl ester 62.4 g of 3-nitro-4-(4-4'-methylanilino)-5-N,N-dimethylaminomethylene-aminosulfonyl benzoic acid methyl ester are dissolved in 1.5 ltr. of dimethylformamide and hydrogenated for 8 hours at 50° C. and under a pressure of 50 atmospheres in the presence of Raney nickel. The catalyst is then separated and the filtrate introduced into ice water while stirring. The melting point is 186°–188° C.

(c)

3-N-pyrrolo-4-(4'-methylanilino)-5-N,N-dimethylaminomethylene-aminosulfonyl benzoic acid methyl ester 0.1 mole of 3-amino-4-(4'-methylanilino)-5-N,N-dimethylaminomethylene-aminosulfonyl benzoic acid methyl ester are dissolved in 400 ml of glacial acetic acid and refluxed. After 15 ml of 2,5-dimethoxytetrahydrofurane have been added, heating is continued for further 30 minutes, the mixture is then introduced into 3 l of ice water while stirring. The precipitated product may be recrystallized from CH₃OH.

Melting point: 169°–173° C.

The product may be converted to 3-pyrrolo-4-(4'-methylanilino)-5-sulfamoyl benzoic acid by saponification with 2 N NaOH, until a limpid solution is obtained, yielding light-yellow crystals by recrystallization from CH₃OH/H₂O and having a melting point of 226°–228° C.

(d) Hydrogenation to obtain 4-(4'-methylanilino)-3(1-pyrrolidinyl)-5-sulfamoyl-benzoic acid The 3-N-pyrrolo-4-(4'-methylanilino)-5-N,N-dimethylamino-methylene-aminosulfonyl benzoic acid methyl ester prepared according to (c) is suspended in methanol as a crude product and hydrogenated at 100° C. and under a pressure of 150 atmospheres, in the presence of Pd/C as a catalyst, for 16 hours. The filtrate is condensed to dryness and heated with 2 N NaOH until a limpid solution is obtained, which is then adjusted to pH 4 by means of 2 N NaOH, and the precipitated product is recrystallized from CH₃OH/H₂O, yielding yellow crystals melting at 188°–191° C.

EXAMPLE 13

3-N-pyrrolo-4-(4'-methylphenoxy)-5-sulfamoylbenzoic acid 17 g of 3-N-pyrrolo-4-(4'-methylphenoxy)-5-N,N-dimethylaminomethylene-aminosulfonyl benzoic acid methyl ester (cf. Example 2c) are suspended in 2 N NaOH and a minor quantity of CH₃OH and refluxed until a limpid solution is obtained. Subsequently, 3-N-pyrrolo-4-(4'-methylphenoxy)-5-sulfamoyl benzoic acid is precipitated from the cold solution by adding 4 N-HCl up to a pH of 3–4. The product is filtered off, washed with water and recrystallized from CH₃OH/H₂O. There are obtained 12.7 g having a melting point of 205°–208° C.

EXAMPLE 14

3-N-pyrrolo-4-(4'-chlorophenoxy)-5-sulfamoyl benzoic acid

The ester of Example 5c is suspended in 2 N NaOH and refluxed until a limpid solution is obtained. Stirring is continued for half an hour and the mixture acidified with 2 N HCl to a pH of 3–4. The precipitated product is isolated, recrystallized from CH₃OH/H₂O+active coal and subsequently recrystallized or precipitated by adding n-hexane to the hot filtered solution in diisopropyl ether. There is obtained a beige powder melting at 209°–214° C.

What is claimed is:

1. The method for treating edema in a patient suffering therefrom which comprises administering to said patient a sali-diuretically effective amount of a compound of the formula

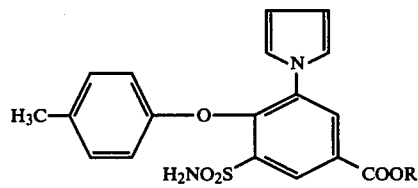

or a pharmaceutically acceptable salt thereof with a base, wherein R is hydrogen or straight-chain or branched alkyl having 1 to 4 carbon atoms.

2. A pharmaceutical composition having salidiuretic activity, in dosage unit form, comprising 0.5 mg to 100 mg of a compound of the formula

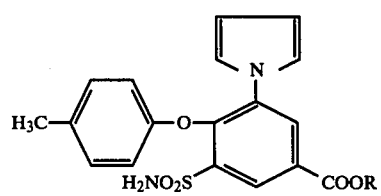

or a pharmaceutically acceptable salt thereof with a base, wherein R is hydrogen or straight-chain or branched alkyl having 1 to 4 carbon atoms.

* * * * *